(12) United States Patent
Frey et al.

(10) Patent No.: US 7,871,218 B2
(45) Date of Patent: Jan. 18, 2011

(54) COUPLING MECHANISM

(75) Inventors: Sebastian Frey, Villingen-Schwenningen (DE); Michael Sauer, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 24 days.

(21) Appl. No.: 12/034,373

(22) Filed: Feb. 20, 2008

(65) Prior Publication Data

US 2008/0199252 A1    Aug. 21, 2008

(30) Foreign Application Priority Data

Feb. 21, 2007    (DE) .................... 10 2007 008 422

(51) Int. Cl.
*F16B 21/06*    (2006.01)
(52) U.S. Cl. ................. 403/328; 403/109.8; 403/322.1; 403/348
(58) Field of Classification Search .............. 403/109.3, 403/109.8, 322.1, 325, 328, 348
See application file for complete search history.

(56) References Cited

U.S. PATENT DOCUMENTS

| | | | | |
|---|---|---|---|---|
| 3,830,579 | A * | 8/1974 | Roe | 403/24 |
| 5,033,777 | A * | 7/1991 | Blenkush | 285/317 |
| 5,090,747 | A * | 2/1992 | Kotake | 285/305 |
| 5,464,300 | A * | 11/1995 | Crainich | 403/322.1 |
| 5,531,140 | A * | 7/1996 | Chow | 81/177.85 |
| 5,695,223 | A * | 12/1997 | Boticki | 285/23 |
| 5,836,781 | A * | 11/1998 | Hyzin | 439/348 |
| 6,024,124 | A * | 2/2000 | Braun et al. | 137/614.03 |
| 6,767,155 | B2 * | 7/2004 | O'Brien et al. | 403/322.1 |
| 6,908,222 | B2 * | 6/2005 | Brunswick et al. | 366/331 |
| 7,066,678 | B2 * | 6/2006 | Huang | 403/321 |
| 7,153,296 | B2 * | 12/2006 | Mitchell | 604/533 |
| 2003/0155765 | A1 * | 8/2003 | Thomas et al. | 285/305 |

FOREIGN PATENT DOCUMENTS

| | | |
|---|---|---|
| DE | 3014116 A1 | 10/1980 |
| DE | 44 25 705 | 1/1996 |
| DE | 197 24 282 | 10/1998 |
| DE | 19712645 C1 | 10/1998 |
| DE | 19844583 A1 * | 4/2000 |

OTHER PUBLICATIONS

German Search Report, May 21, 2007, 4 pages.
European Search Report, EP08002500, May 13, 2009, 6 pages.

* cited by examiner

*Primary Examiner*—Joshua T Kennedy
(74) *Attorney, Agent, or Firm*—St. Onge Steward Johnston & Reens LLC

(57) ABSTRACT

A coupling mechanism, in particular for medical instruments, having a coupler plug and a coupler socket for inserting the coupler plug, where the coupler socket and coupler plug can be secured to one another by at least one spring-loaded catch connection, where the catch connection can be actuated by a safety mechanism and can be released by the coupler plug inserted into the coupler socket. To create a coupling mechanism that is simple to operate and ensures secure catching connection of the components and that are to be connected with one another, the safety mechanism should be configured as a spring-loaded catch element positioned in the coupler socket.

9 Claims, 4 Drawing Sheets

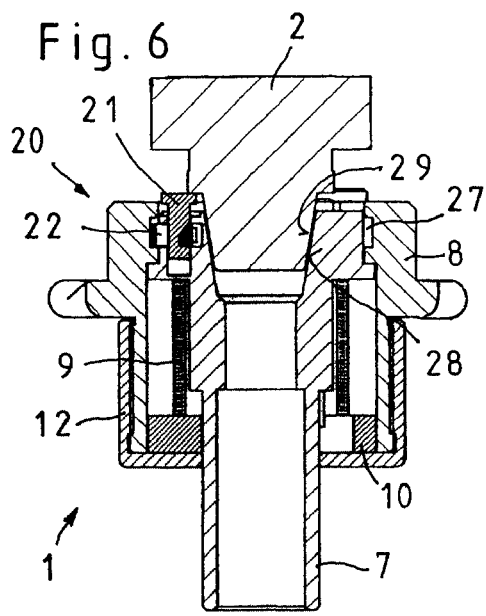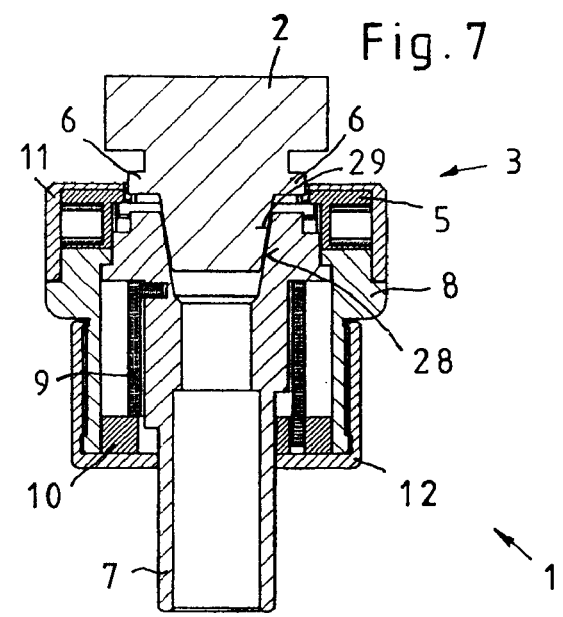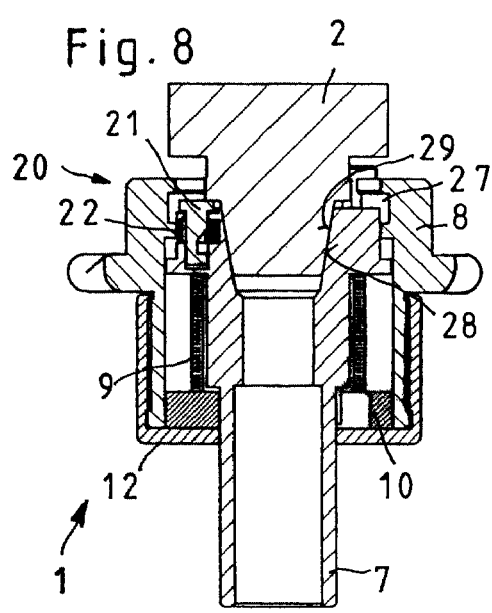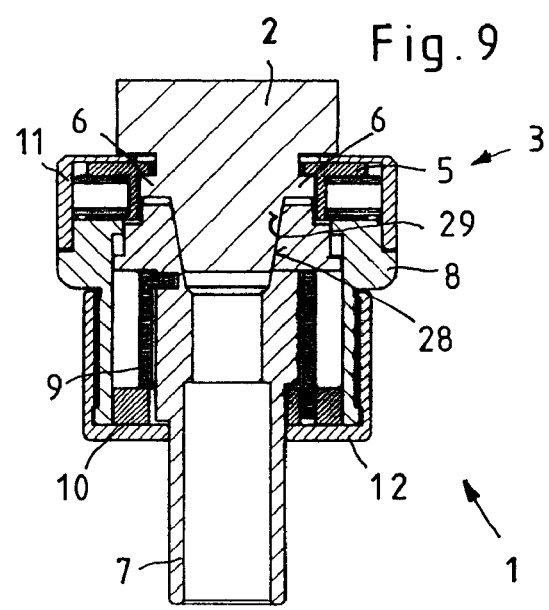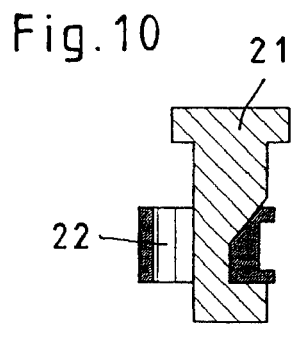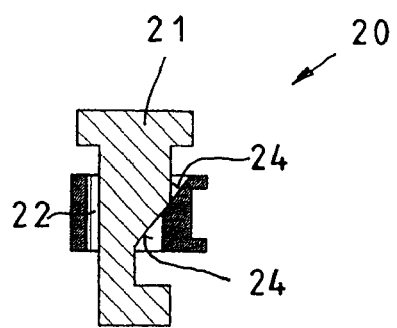

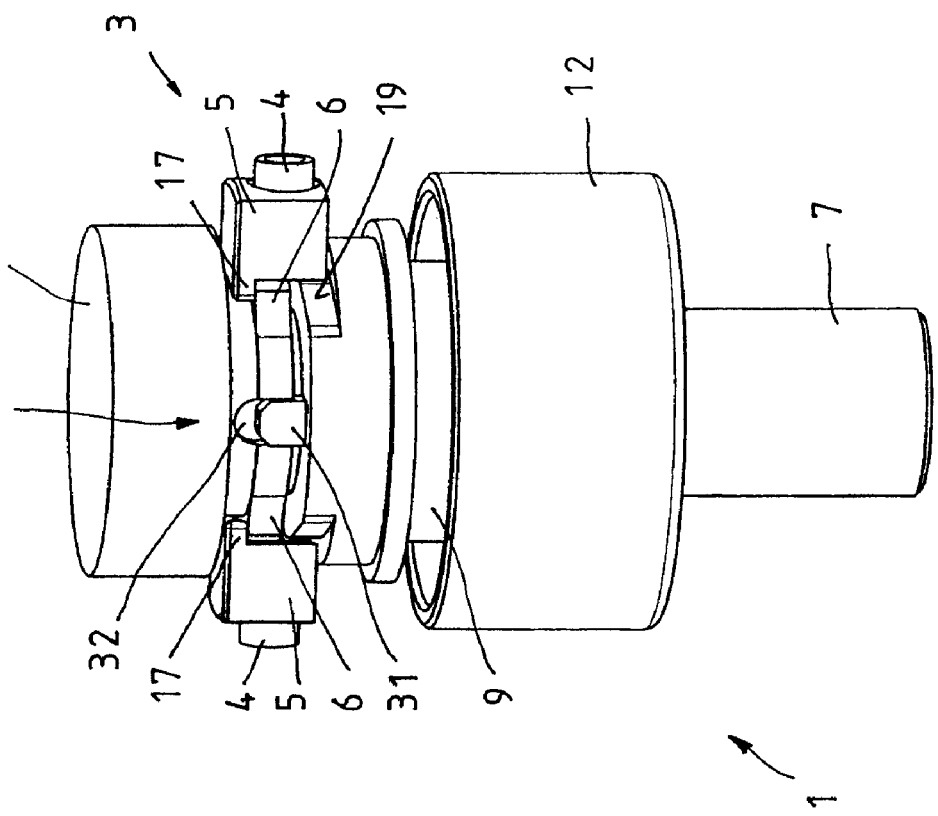
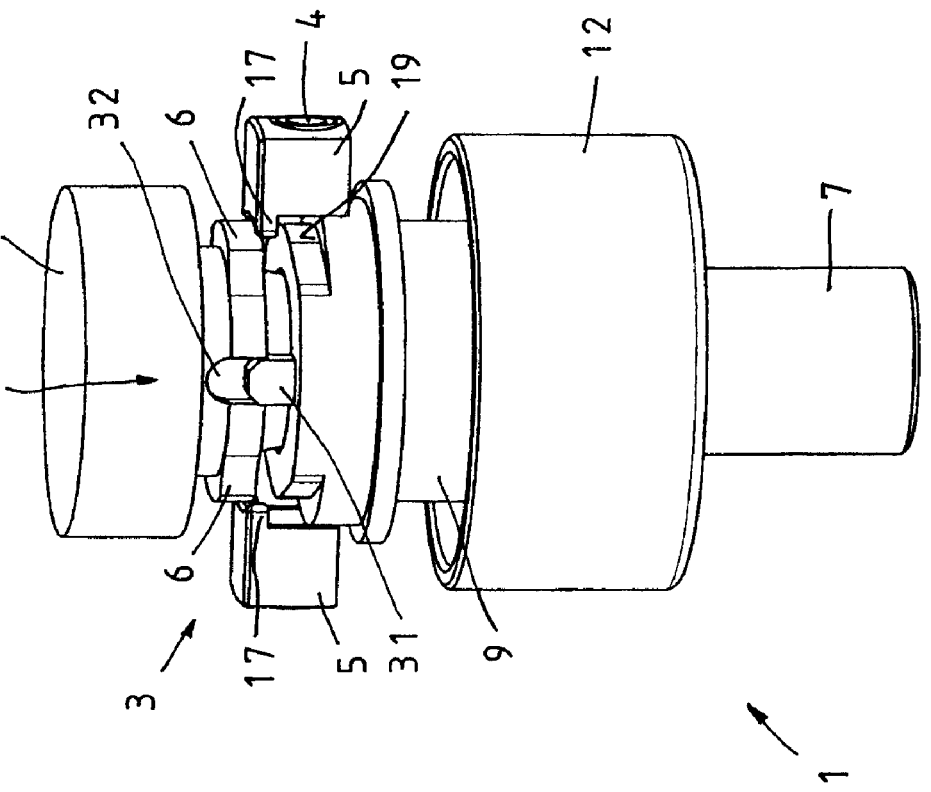

COUPLING MECHANISM

CROSS-REFERENCE TO RELATED APPLICATIONS

The present application claims priority of German patent application No. 10 2007 008 422.8 filed on Feb. 21, 2007, the content of which is incorporated herein by reference.

FIELD OF THE INVENTION

The invention relates to a coupling mechanism, in particular for medical instruments, having a coupler plug and a coupler socket for inserting the coupler plug, such that the coupler socket and the coupler plug can be secured to one another by means of at least one spring-loaded catch connection, where the catch connection can be actuated by a safety mechanism and can be released by the coupler plug inserted into the coupler socket.

BACKGROUND OF THE INVENTION

A generic coupling mechanism is known, for instance, from DE 44 25 705 C2. This known coupling mechanism is a component of an endoscopic instrument, wherein the coupler socket is configured on the proximal end of the instrument and the coupler plug is a component of a second instrument that is to be connected with this endoscopic instrument. This known coupling mechanism consists of a bayonet coupling and a spring-loaded catch element by which the two components can be fixed in relation to one another. This known coupling mechanism has thoroughly proven itself in the art; however, the structure with a bayonet coupling and a catch element is complex. In addition it requires a separate manual rotation of a swivel in order to fix the two components in relation to one another.

Consequently, it is the object of the invention to create a coupling mechanism of the aforementioned type which is simple to operate and ensures a secure catching of the components that are to be connected to one another.

SUMMARY OF THE INVENTION

This object is met according to the invention in that the safety mechanism is configured as a spring-loaded catching element that is mounted in the coupler socket.

Because of the inventive configuration of the safety mechanism according to the invention as a spring-loaded catching element mounted in the coupler socket, on the one hand any accidental locking is prevented and on the other hand an automatic locking of the inserted coupler socket is ensured if the catch connection is actuated by actuation of the safety mechanism. This embodiment has the advantage that the actuation of the catch connection and the coupling of the components, the coupler plug and coupler socket, can occur in time sequence in one work step, so that connection of the components can be managed simply and securely.

According to a practical embodiment of the invention, the catching element of the inventive safety mechanism consists of an axially slidable pin and a radially slidable clamping element that is in active connection with the pin, where the clamping element is pre-tensed by a spring element in the direction that blocks the safety mechanism. Because of the spring pre-tensing of the clamping element of the safety mechanism it can be ensured that the catch connection remains deactivated and thus prevents accidental locking as long as the safety mechanism has not previously been actuated appropriately.

To facilitate the cooperation of the axially slidable pin with the radially slidable clamping element, it is proposed with the invention that mutually corresponding starter slopes should be configured on the pin and on the clamping element.

It is further proposed with a preferred embodiment of the invention that the catch connection should consist of at least one catch hook that is positioned on the coupler socket and is spring-loaded by at least one spring element in the catching direction, and of at least one catch insert positioned on the coupler plug for inserting the at least one catch hook. Because of the inventive design of the coupling mechanism it is possible, after actuation of the catch connection by actuating the safety mechanism, that the two components that are to be connected with one another can be connected to one another and insulated from gas and liquid simply by being plugged together. No additional mechanical activity or the use of a tool is required with the inventive mechanism.

According to a practical embodiment of the invention, the coupler socket comprises an inner sleeve and an outer sleeve that, at least partly, coaxially surrounds the inner sleeve, where the inner sleeve and outer sleeve are coupled together so that they can rotate with respect to one another by means of a spring element, in particular a pressure torsion spring. The spring element here, first, ensures axial tolerance compensation between the coupler plug that is to be inserted into the coupling socket and the catch elements of the catch connection and, second, the spring element allows a reciprocal rotatability of the inner and outer sleeves with respect to one another.

For configuring the inventive catch hooks, notches pointed inward are configured on the notch hooks and, when notched with the coupler plug, are configured as studs that reach around the coupler plug. Coupling and uncoupling of the catch hooks of the coupler socket with the notch recesses on the coupler plug can be facilitated, according to the invention, if the notch hooks are mounted so that they can slide radially in the outer sleeve and, when notched with the coupler plug, are contiguous with a contact surface of the inner sleeve.

To separate the two components connected with one another by means of the inventive coupling mechanism, the notching connection can be undone again by means of a release mechanism that is in active connection with the at least one notch hook.

According to a practical embodiment for configuring the release mechanism, it is proposed that for configuring the release mechanism the contact surface of the inner sleeve, with which the catch hooks are contiguous when notched, should be configured as non-rounded sliding track. Because of the reciprocal rotatable mobility of the inner sleeve and outer sleeve with respect to one another, the catch hooks move along this sliding track during reciprocal rotation of the components and, because of the non-rounded configuration of the sliding track, they can be pushed from inside toward the outside until the notches again release the studs of the coupler plug and the inner and outer sleeves are pressed apart by the spring action.

It is further proposed with the invention that cams extending radially outward should be configured on the outer sleeve. Thanks to these cams the operating of the coupler socket, particularly the reciprocal rotation of the components, inner sleeve and outer sleeve, are facilitated because, like handle grips, they facilitate the gripping of the outer sleeve.

It is finally proposed with the invention that mutually corresponding guide and/or centering elements should be configured on the coupler socket in order to ensure exact, rotation-proof siting of the components with respect to one another and consequently to make possible a rapid, perfect coupling by means of the catch connection.

In addition, the invention relates to a coupler socket for inserting a coupler plug of a coupling mechanism, in particular for medical instruments, so that the coupler socket and coupler plug can be secured to one another by at least one spring-loaded catch connecting. Because the coupler plug in practical embodiments of this type of medical coupling mechanisms is often configured on a standard instrument that can be put to multiple uses, for instance an endoscope lens system, which can be coupled with various other medical instruments by means of a coupler socket, the inventive coupler socket is characterized in that the catch connection can be actuated by means of a safety mechanism in order thus, in addition to ease of operation, to ensure a safe, well-stabilized, and gas and liquid-proof catching connection of the components.

Further characteristics and advantages of the invention can be seen from the appended illustrations, in which an embodiment of an inventive coupling mechanism is depicted in exemplary manner, without restricting the invention to this embodiment.

BRIEF DESCRIPTION OF THE DRAWINGS

FIG. 6 shows a longitudinal section along the line VI-VI of FIG. 2, but with the coupler plug.

FIG. 7 shows a longitudinal section along the line VII-VII of FIG. 2, but with the coupler plug and covering cap.

FIG. 8 shows a longitudinal section along the line VIII-VIII of FIG. 4 but with the coupler plug.

FIG. 9 shows a longitudinal section along the line IX-IX of FIG. 4, but with the coupler plug and covering cap.

FIG. 10 shows an enlarged view of detail X of FIG. 6 in the blocking and releasing positions.

FIG. 11 shows a perspective side view of the assembled coupling mechanism of FIG. 1 not in catching connection, but without covering cap and outer sleeve.

FIG. 12 shows a view as in FIG. 11 but with the coupling mechanism in catching connection.

DETAILED DESCRIPTION OF THE INVENTION

Figure 1:
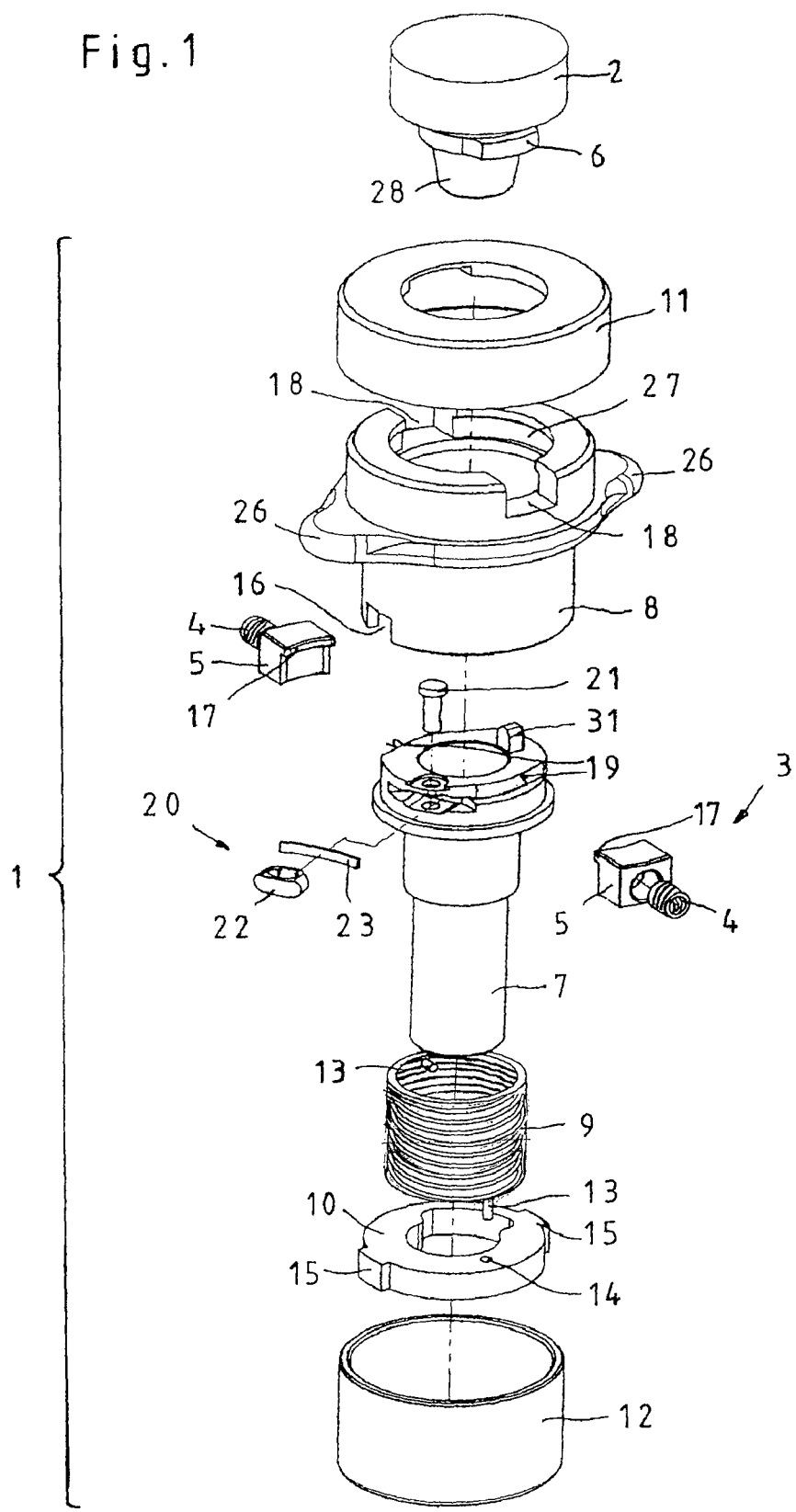
FIG. 1 shows an explosion view of an inventive coupling mechanism.

The coupling mechanism depicted in FIGS. 1 through 12 consists essentially of a coupler socket 1 and a coupler plug 2 that can be secured by catching in the coupler socket 1 by means of a catch connection 3, where the catch connection 3 in the illustrated embodiment consists of two notch hooks 5, spring loaded in the notching direction by one spring element 4 each, and two catch recesses 6, positioned on the coupler plug 2 for inserting the at least two catch hooks 5. In the illustrated embodiment the catch recesses 6 are configured as webs 6 distanced radially outward from the coupler plug 2.

As can be seen from the illustrations, the catch connection 3 is configured in such a way that the catch hooks 5 are positioned on the coupler socket 1 and the catch recesses 6 are positioned on the coupler plug 2.

Coupling mechanisms of this type are preferably used in order to connect to one another two medical instruments, such as an endoscopic instrument and an endoscope eyepiece, so that they are insulated against gas and liquid.

As can be seen in particular from the explosion view in FIG. 1, the coupler socket 1 consists essentially of an inner sleeve 7, an outer sleeve 8 that can be mounted onto the inner sleeve 7 from the coupling side and that coaxially surrounds the inner sleeve, a spring element 9 that can be pushed up onto the inner sleeve 7 from the free lower end upward and surrounds the inner sleeve 7 coaxially, as well as a ring 10 that can likewise be pushed up from the free lower end upward onto the inner sleeve 7. This multi-part coupling socket 1 can be closed off on both sides by an upper covering cap 11 that can be mounted on the outer sleeve 8 as well as a lower closing cap 12 that can be pushed upward from the free lower end onto the inner sleeve 7.

As can also be seen from FIG. 1 in juxtaposition with FIGS. 7 and 9, the inner sleeve 7 and the outer sleeve 8 are coupled with one another so that they can rotate with respect to one another by means of the spring element 9 configured as a pressure and torsion spring. For this purpose two pins 13 are formed on the spring element 9 and serve to secure the spring element 9 on the one hand in a pin recess 14 on the inner sleeve 7 and on the other hand in a pin recess 14 on the ring 10. In addition, protrusions 15 are configured on the ring 10 radially distanced outward and, when the coupling socket 1 is assembled, engage in corresponding recesses 16 in the outer sleeve 8.

The actual coupling of the coupler socket 1 with the coupler plug 2 by means of the catch connection 3 take place by means of notches 17 configured on the notch hooks 5 and pointing inward, which when catch-connected grip around the catch recess 6 of the coupler plug 2, as can be seen from FIGS. 7, 9, and 12.

In order to be able to displace the catch hooks between a position that connects the coupler parts 1 and 2 with one another and a position that releases them again, the catch hooks 5 are positioned so that they can slide radially in guides 18 of the outer sleeve 8 in such a way that the spring elements 4 that pre-tense the catch hook 5 in the notching direction are supported, on the one hand, on the inside of the covering cap 11 and, on the other hand, are contiguous with the catch hooks 5, in order to press them radially inward until the notches 17 of the catch hooks 5, when catch-connected with the coupler plug 2, grip behind the webs 6 of the coupler plug 2. The sliding of the catch hooks 5 radially inward, when catch-connected with the coupler plug 2, is restricted by the fact that the catch hooks 5 on the inside come into connect with a contact surface 19 of the inner sleeve 7. This contact surface 19 of the inner sleeve 7, as can be seen in particular from FIG. 1, is configured as a non-rounded sliding track.

As a particularity the illustrated coupling mechanism comprises a safety mechanism 20 by means of which the catch connection 3 can be actuated. The safety mechanism 20 serves to prevent any accidental catching of the catch connection 3 without an instrument inserted. As can be seen from FIGS. 1, 3, 5, 6, and 8 and in particular from FIG. 10, the safety mechanism 20 in the illustrated embodiment is configured as an axially slidable pin 21 and a radially slidable clamping element 22 that is in active connection with the pin 21, where the clamping element 22 is pre-tensed in the direction blocking the safety mechanism 20 by means of a spring element 23 advantageously configured as a spring steel sheet.

To facilitate the interplay between the axially slidable pin 21 and the radially slidable clamping element and to simplify conversion of the safety mechanism 20 from the position that blocks the catch connection 2 into the position that releases the catch connection 3, corresponding run-up slopes 24 are configured on contact surfaces of the pin 21 and of the clamping element 22 that are in active connection with one another, which slopes preferably form an a 45-degree angle, so that the pin 21 on coming in contact against the clamping element 22 automatically presses the clamping element 22 radially inward.

To separate the two components 1 and 2 that are connected with one another by means of the coupling mechanism, the catch connection 3 can be released again by means of a release mechanism 25 that is in active connection with the catch hooks 5.

As can be seen in particular from FIGS. 1, 2, 4, 11, and 12, the release mechanism 25 consists of the contact surface 19 of the inner sleeve 7, configured as a non-rounded sliding track, and of cams 26 configured on the outer sleeve 8 and extending radially outward, by means of which cams the outer sleeve 8 can be rotated with respect to the inner sleeve 7. On rotating the outer sleeve 8, the catch hooks 5 that, when the coupling mechanism is catch-connected, are in contact with the contact surface 19 move along this non-rounded sliding track and during this motion are pressed radially outward until the notches 17 of the catch hooks 5 no longer reach around the webs 6 of the coupler plug 2 and release the coupling of the components 1 and 2 as well as the inner sleeve 7.

The overview and the actuation of the coupling mechanism is elucidated hereafter by reference to the appended illustrations, FIGS. 1 and 6-9:

In the first assembly step, the safety mechanism 20, consists of the pin 21, the clamping element 22, and the spring element 23, is secured on the inner sleeve 7.

Then, from the lower end of the inner sleeve 7 at a distance from the coupling, first the spring element configured as a pressure and torsion spring is pushed onto the inner sleeve 7 until the pin 13 of the spring element 9 engages in the pin recess 14 of the inner sleeve 7. In the next step, likewise from the lower end of the inner sleeve 7 at a distance from the coupling, the ring 10 is pushed onto the inner sleeve 7 until the pin 13 of the spring element 9 engages in the pin recess 14 of the ring 10.

Now, on this assembly, from the upper end of the inner sleeve 7 close to the coupling, the outer sleeve 8 is placed on the inner sleeve 7 until the protrusions 15 formed on the ring 10 engage in the recesses 16 of the outer sleeve 8. This coupling of the inner sleeve 7 with the outer sleeve 8, which can rotate with respect to one another by means of the spring element 9, is held together by the closing cap 12 that can be pushed from the free lower end onto the inner sleeve 7 and screwed onto the outer sleeve 8.

In the next step of the assembly, the catch hooks 5 and spring elements 4 are inserted into the guides 18 of the outer sleeve 8 and then, from the coupling end, the upper cover cap 11 is placed on the outer sleeve 8 and connected with it, for example by soldering, in such a way that the spring elements 4 are supported on the rear on the inside of the covering cap 11 and the catch hooks 5 press radially inward against the inner sleeve 1.

With the coupling socket 1 in this assembled state, the spring element 23 of the safety mechanism presses the radially slidable clamping element 22 radially outward into a relief groove 27 in the outer sleeve 8, as is shown in FIG. 6. In this position the safety mechanism 20 blocks the catch connection 3 against accidental catching.

The coupling mechanism at this point is ready to make possible the catching connection between the coupler plug 2 and the coupler socket 1. In the illustrated embodiment the parts of the coupler plug 2 and coupler socket 1 that are to be joined into one another are configured as a cone 28 and countercone 29. Other shapes such as tubular coupling pieces are also possible of course.

To ensure an exactly positioned and rotation-proof placement of the components, coupler socket 1 and coupler plug 2, with respect to one another, mutually corresponding guide and/or centering elements 30, as can be seen in FIGS. 11 and 12, are configured on the coupler plug 2 and on the coupler socket 1, which elements are configured in the illustrated embodiment as a centering pin 31 and a socket groove 32.

Starting from the initial position illustrated in FIGS. 6 and 11, in which the coupler plug 2 and the coupler socket 1 are aligned with one another by the guide and/or centering elements 28 and the coupling plug 2 is contiguous with the underside of the catch recess 6 on the pin 21 of the safety mechanism 20, the coupler plug 2 is subsequently pressed downward into the coupler socket 1 for catching with the coupler socket 1. This axial pressure exerted by the coupler pug 2 on the pin 21 of the safety mechanism 20 causes, as shown in FIG. 10, the clamping element 22 to be pressed radially inward by the mutually contiguous start-up slopes 24 of the pin 21 and of the clamping element 22 and causes the relief groove of the outer sleeve 8 to be released again.

This unlocking of the safety mechanism 20 has the effect that the coupler plug 2 can be pressed farther into the coupler socket 1 and the catch connection 3 is actuated. As soon as the coupler plug 2 has penetrated sufficiently deep into the coupler socket 1, the catch hooks 5 that are pre-tensed in the catching direction by the spring elements 4 are pressed radially inward until the notches 17 of the coupler socket 1 reach around the webs 6 of the coupler plug 2 and fix the coupler plug 2 in the coupler socket 1 so that it is insulated against gas and liquid.

Figure 2:
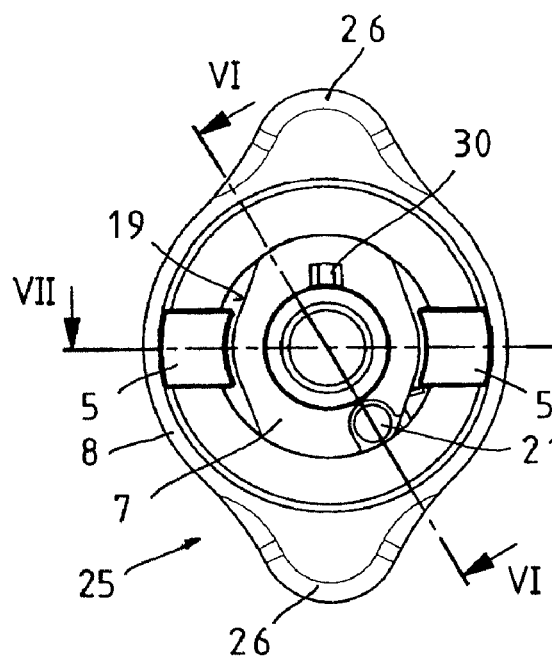
FIG. 2 shows an overhead view of the assembled coupling mechanism of FIG. 1, in not catch-connected, but without covering cap an coupler plug.
Figure 3:
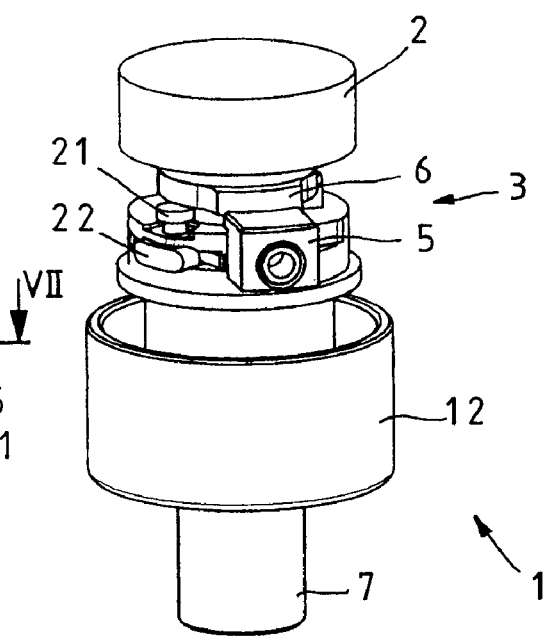
FIG. 3 shows a perspective side view of the coupling mechanism of FIG. 2 but with the coupler plug, but without outer sleeve.
Figure 4:
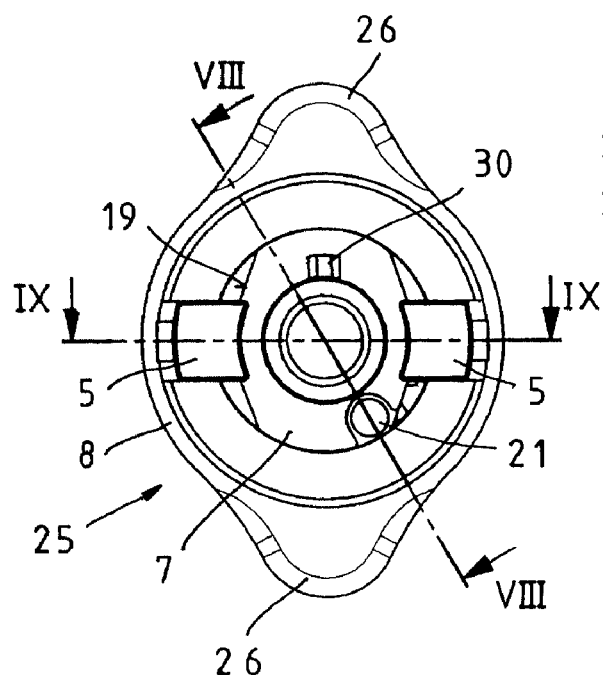
FIG. 4 shows a view as in FIG. 2 but without covering cap; however it includes the coupling mechanism in catch-connected position.
Figure 5:
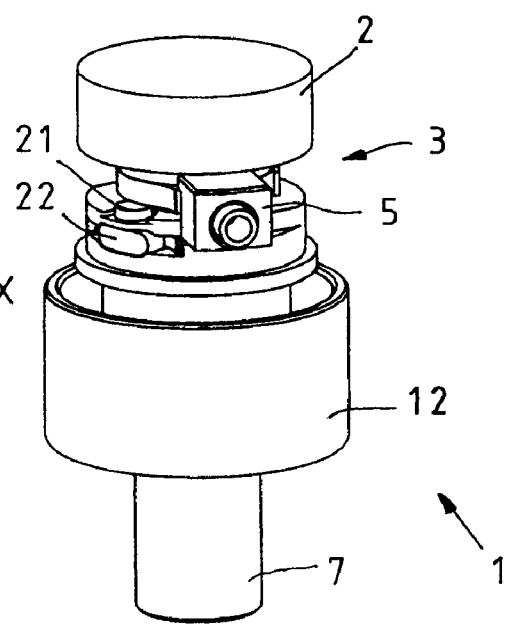
FIG. 5 shows a perspective side view of the coupling mechanism of FIG. 4 but with the coupler plug, but without outer sleeve.

To release the catch connection, the outer sleeve 8 is rotated by the two cams 26, especially as illustrated in FIGS. 2 and 4, with respect to the inner sleeve 7 until the catch hooks 5 contiguous with the contact surface 19 of the inner sleeve 7 are pressed radially outward by the non-rounded sliding track of the contact surface 19 and the notches 17 of the catch hooks 5 engage with the webs 6 of the coupler socket 2.

Because of the spring element 9, configured as a pressure and torsion spring, which on the one hand makes possible the rotation of the inner sleeve 7 and the outer sleeve 8 with respect to one another and on the other hand serves as an axial tolerance balance in the catching with the coupler plug 2, the outer sleeve 8 is automatically rotated back into the starting position again because of the torsion force as soon as the catch connecting 3 is released. This counter-rotation of the outer sleeve 8 causes an axial lifting of the coupler plug 2 out of the coupler socket 1.

In this unlocked position the spring element 23 presses the clamping element 22 of the safety mechanism 20 radially outward again into the relief groove 27 of the outer sleeve 8, so that the pin 21 again assumes the position seen in FIG. 6 and the safety mechanism 20 blocks the catch connection 3.

A coupling mechanism of this design is distinguished in that causes a secure connection, insulated against gas and liquid, by merely pressing together the components 1 and 2 that are to be connected to one another.

What is claimed is:

1. A coupling mechanism comprising:
a coupler plug having at least one catch recess,
a coupler socket for receiving the coupler plug,
at least one spring-loaded catch connection comprising at least one horizontally spring-loaded catch hook positioned on the coupler socket corresponding to the at least one catch recess for connecting said coupler socket and said coupler plug to one another, and
a safety mechanism comprising a spring-loaded catch element positioned in the coupler socket and consisting of an axially slidable pin and a radially slidable clamping element that is in active connection with the pin, wherein the clamping element is pre-tensed by a spring element in a direction that prevents actuation of the catch connection,
wherein the insertion of the coupler plug into the socket and against the pin actuates said safety mechanism, causing the clamping element to be pressed radially inwardly, thus allowing the coupler plug to be pressed further into the socket to actuate the catch connection.

2. The coupling mechanism of claim 1, further comprising mutually corresponding start-up slopes on the pin and on the clamping element.

3. The coupling mechanism of claim 1, wherein the coupler socket comprises an inner sleeve and an outer sleeve that coaxially surrounds the inner sleeve at least partly, where the inner sleeve and the outer sleeve are coupled with one another so that they can rotate with respect to one another by means of a pressure spring element.

4. The coupling mechanism of claim 3, further comprising the at least one catch hook being radially slidable in the outer sleeve and, when catch-connected with the coupler plug, being contiguous with a contact surface of the inner sleeve.

5. The coupling mechanism of claim 3, wherein the catch connection can be released by means of a release mechanism that is in active connection with the at least one catch hook.

6. The coupling mechanism of claim 5, further comprising a contact surface on the inner sleeve, with which the catch hooks are contiguous when catch-connected, comprising a non-rounded sliding track.

7. The coupling mechanism of claim 3, further comprising extending radially outward are configured on the outer sleeve.

8. The coupling mechanism of claim 1, further comprising at least one notch pointing inward on the at least one catch hook, said at least one notch, when catch-connected with the coupler plug, grips said at least one catch recess on the coupler plug.

9. The coupling mechanism of claim 1, further comprising mutually corresponding guide and/or centering elements are configured on the coupler plug and coupler socket respectively.

* * * * *